United States Patent
Hasegawa et al.

(10) Patent No.: US 8,558,431 B2
(45) Date of Patent: Oct. 15, 2013

(54) OUTPUT ADJUSTMENT CIRCUIT, ULTRASONIC TRANSDUCER DEVICE COMPONENT, AND ULTRASONIC TRANSDUCER DEVICE

(75) Inventors: Hiroshi Hasegawa, Hamura (JP); Takehiko Ishizuka, Hamura (JP); Satoshi Domon, Hamura (JP)

(73) Assignee: Kaijo Corporation, Tokyo (JP)

( * ) Notice: Subject to any disclaimer, the term of this patent is extended or adjusted under 35 U.S.C. 154(b) by 418 days.

(21) Appl. No.: 12/937,625

(22) PCT Filed: Jun. 26, 2009

(86) PCT No.: PCT/JP2009/061740
§ 371 (c)(1),
(2), (4) Date: Oct. 13, 2010

(87) PCT Pub. No.: WO2010/035560
PCT Pub. Date: Apr. 1, 2010

(65) Prior Publication Data
US 2011/0030741 A1 Feb. 10, 2011

(30) Foreign Application Priority Data
Sep. 26, 2008 (JP) .................. 2008-247971

(51) Int. Cl.
*H01L 41/08* (2006.01)
*B08B 3/12* (2006.01)

(52) U.S. Cl.
CPC ..................................... *B08B 3/12* (2013.01)
USPC .......................................... 310/334; 310/317

(58) Field of Classification Search
CPC ................ B06B 1/0261; B08B 3/12
USPC ........................ 310/334; 134/1, 1.3
See application file for complete search history.

(56) References Cited

U.S. PATENT DOCUMENTS

| 5,462,604 A | 10/1995 | Shibano et al. |
| 2011/0254519 A1* | 10/2011 | Hasegawa et al. ............ 323/234 |
| 2012/0270177 A1* | 10/2012 | Nakashima et al. ............ 433/86 |

FOREIGN PATENT DOCUMENTS

| JP | 6-126249 | 5/1994 |
| JP | 6-296942 | 10/1994 |
| JP | 2001-246338 | 9/2001 |

OTHER PUBLICATIONS

International Search Report issued Sep. 29, 2009 in International (PCT) Application No. PCT/JP2009/061740.

* cited by examiner

*Primary Examiner* — J. San Martin
(74) *Attorney, Agent, or Firm* — Wenderoth, Lind & Ponack, L.L.P.

(57) ABSTRACT

An ultrasonic transducer device component changes a transducer with another one having the same frequency or a different frequency without adjustment inside a generator main body or a change of the generator main body. The ultrasonic transducer device component includes a connection unit for use in applying ultrasonic transducer to cleaning fluid for cleaning objects, and for connection with a generator main body that generates an ultrasonic vibration signal; and a transducer connected to a connection unit. The connection unit includes an output transformer for adjusting an output of the ultrasonic vibration signal; a coil capacitor electrically connected to the output transformer; and a current detector electrically connected to the coil capacitor.

1 Claim, 8 Drawing Sheets

DISTRIBUTION OF VIBRATION AMPLITUDE

OUTPUT ADJUSTMENT CIRCUIT, ULTRASONIC TRANSDUCER DEVICE COMPONENT, AND ULTRASONIC TRANSDUCER DEVICE

BACKGROUND OF INVENTION

1. Technical Field

The present invention relates to an ultrasonic transducer device, etc. which apply ultrasonic transducer to cleaning fluid that cleans objects to be cleaned, and in particular, relates to an output adjustment circuit, an ultrasonic transducer device component and an ultrasonic transducer device, etc. which can change a transducer with another one having the same frequency or a different frequency without adjustment inside a generator main body or a change of the generator main body.

2. Background Art

FIG. 8 shows a schematic diagram illustrating a configuration of a conventional ultrasonic transducer device. This ultrasonic transducer device constitutes a part of an ultrasonic washing machine, and is a device for applying ultrasonic transducer to cleaning fluid (not shown) when cleaning objects to be cleaned (not shown) by said cleaning fluid. This device comprises a generator main body 38 and a transducer 39 connected to this generator main body 38 by connectors 48 and 49.

Said ultrasonic washing machine is an apparatus in which an ultrasonic vibration signal is generated from the generator main body 38, the ultrasonic vibration signal is transmitted to the transducer 39, and the ultrasonic vibration generated by the transducer 39 is applied to said cleaning fluid, thereby cleaning objects to be cleaned.

The generator main body 38 includes a signal generator 41, and this signal generator 41 is electrically connected to a driver 42. The driver 42 is electrically connected to an amplifier 43, and the amplifier 43 is electrically connected to an output transformer 44. The output transformer 44 is electrically connected to a coil capacitor 45, and the coil capacitor 45 is electrically connected to a current detector 46. Each of the current detector 46 and the coil capacitor 45 is electrically connected to a voltage detector 47, and the voltage detector 47 is electrically connected to a connector 48. Each of the signal generator 41, the driver 42, the amplifier 43, the current detector 46 and the voltage detector 47 is electrically connected to a control part 40.

SUMMARY OF THE INVENTION

Incidentally, the transducer 39 differs in electrical characteristics largely depending on a shape and a frequency thereof. Therefore, it is necessary to change a driving circuit of the generator main body 38 greatly for every type of the transducer 39. Since variations in the electrical characteristics depending on individual differences exist even if the type of the transducer 39 is the same, in the case of changing the transducer 39, a part where adjustment is needed inside the generator main body 38 arises.

Thus, in the conventional ultrasonic transducer device mentioned above, when the transducer has trouble, only by changing the faulty transducer with another one having the same frequency, the repair can not be completed, and the adjustment inside the generator main body 38 is required at the same time of the a change of the transducer 39. When changing an ultrasonic frequency in connection with cleaning recipe alterations, for example, the frequency cannot be changed only by changing the transducer currently used with another one of a frequency different therefrom, and it is also required to change the generator main body 38 at the same time of the change of the transducer 39.

The present invention has been made in view of the above circumstances, and an object thereof is to provide an output adjustment circuit, an ultrasonic transducer device component and an ultrasonic transducer device, etc. which can change a transducer with another one having the same frequency or a different frequency without adjustment inside a generator main body or a change of the generator main body.

In order to solve the above problems, the output adjustment circuit according to the present invention is the circuit for use in applying ultrasonic transducer from a transducer to cleaning fluid for cleaning objects to be cleaned, said circuit being formed detachably in a generator main body for causing said transducer to generate an ultrasonic vibration signal.

Said output adjustment circuit can also comprise:

an output transformer for adjusting an output of said ultrasonic vibration signal;

a coil capacitor electrically connected to said output transformer; and a current detector electrically connected to said coil capacitor.

An ultrasonic transducer device component comprises:

a connection unit for use in applying ultrasonic transducer to cleaning fluid for cleaning objects to be cleaned, and for connection with a generator main body that generates an ultrasonic vibration signal; and a transducer connected to said connection unit, wherein said connection unit includes:

an output transformer for adjusting an output of said ultrasonic vibration signal;

a coil capacitor electrically connected to said output transformer; and a current detector electrically connected to said coil capacitor.

As for an ultrasonic transducer device according to the present invention, the ultrasonic transducer device for applying ultrasonic transducer to cleaning fluid for cleaning objects to be cleaned, comprises:

a generator main body that generates an ultrasonic vibration signal;

a connection unit detachably connected to said generator main body; and a transducer connected to said connection unit, wherein said connection unit includes:

an output transformer for adjusting an output of said ultrasonic vibration signal;

a coil capacitor electrically connected to said output transformer; and a current detector electrically connected to said coil capacitor.

As for an ultrasonic transducer device according to the present invention, the ultrasonic transducer device for applying ultrasonic transducer to cleaning fluid for cleaning objects to be cleaned, comprises:

a generator main body that generates an ultrasonic vibration signal in any mode of a first to a third mode;

a connection unit of any of a first to a third connection unit detachably connected to said generator main body; and a transducer connected to any of said connection units, wherein said first to third connection units each include:

an output transformer for adjusting an output of said ultrasonic vibration signal;

a coil capacitor electrically connected to said output transformer; and a current detector electrically connected to said coil capacitor; and wherein when the ultrasonic vibration signal is caused to be generated by said generator main body in said first mode, said first connection unit is connected to said generator main body;

when the ultrasonic vibration signal is caused to be generated by said generator main body in said second mode, said second connection unit is connected to said generator main body; and when the ultrasonic vibration signal is caused to be generated by said generator main body in said third mode, said third connection unit is connected to said generator main body.

In the ultrasonic transducer device according to present invention, it is also possible that said connection unit includes a voltage detector, and that said voltage detector is electrically connected to said current detector and said coil capacitor.

As for an ultrasonic transducer device according to the present invention, the ultrasonic transducer device for applying ultrasonic transducer to cleaning fluid for cleaning objects to be cleaned, comprises:

a generator main body that generates an ultrasonic vibration signal in any mode of a first to a third mode;

a change-over switch electrically connected to said generator main body;

a first to a third connection circuit electrically connected to said change-over switch;

a transducer electrically connected to said first to third connection circuits and said change-over switch; and a control part controlling said change-over switch, wherein said first to third connection circuits each include:

an output transformer for adjusting an output of said ultrasonic vibration signal;

a coil capacitor electrically connected to said output transformer; and a current detector electrically connected to said coil capacitor, and wherein, when the ultrasonic vibration signal is caused to be generated by said generator main body in said first mode, said control part controls said change-over switch so that said first connection circuit is connected to said generator main body and said first connection circuit is connected to said transducer;

when the ultrasonic vibration signal is caused to be generated by said generator main body in said second mode, said control part controls said change-over switch so that said second connection circuit is connected to said generator main body and said second connection circuit is connected to said transducer; and when the ultrasonic vibration signal is caused to be generated by said generator main body in said third mode, said control part controls said change-over switch so that said third connection circuit is connected to said generator main body and said third connection circuit is connected to said transducer.

As for an ultrasonic transducer device to according to the present invention, the ultrasonic transducer device for applying ultrasonic transducer to cleaning fluid for cleaning objects to be cleaned, comprises:

a generator main body that generates an ultrasonic vibration signal in any of a first to a third frequency;

a change-over switch electrically connected to said generator main body;

a first to a third connection circuit electrically connected to said change-over switch;

a first transducer electrically connected to said first connection circuit;

a second transducer electrically connected to said second connection circuit;

a third transducer electrically connected to said third connection circuit; and a control part controlling said change-over switch, wherein said first to third connection circuits each include:

an output transformer for adjusting an output of said ultrasonic vibration signal;

a coil capacitor electrically connected to said output transformer; and a current detector electrically connected to said coil capacitor, and wherein when said first transducer is caused to transduce at said first frequency, said control part controls said change-over switch so that said first connection circuit is connected to said generator main body;

when said second transducer is caused to transduce at said second frequency, said control part controls said change-over switch so that said second connection circuit is connected to said generator main body; and when said third transducer is caused to transduce at said third frequency, said control part controls said change-over switch so that said third connection circuit is connected to said generator main body.

In the ultrasonic transducer device according to the present invention, it is also possible that said generator main body includes:

a signal generator;

a driver electrically connected to said signal generator;

an amplifier electrically connected to said driver; and a control part electrically connected to each of said signal generator, said driver and said amplifier.

As described above, according to the present invention, it is possible to provide an output adjustment circuit, an ultrasonic transducer device component and an ultrasonic transducer device, etc. which can change a transducer with another one having the same frequency or a different frequency without adjustment inside a generator main body or a change of the generator main body.

DETAILED DESCRIPTION OF THE INVENTION

Hereinafter, with reference to figures, embodiments according to the present invention will be described.

First Embodiment

Figure 1:
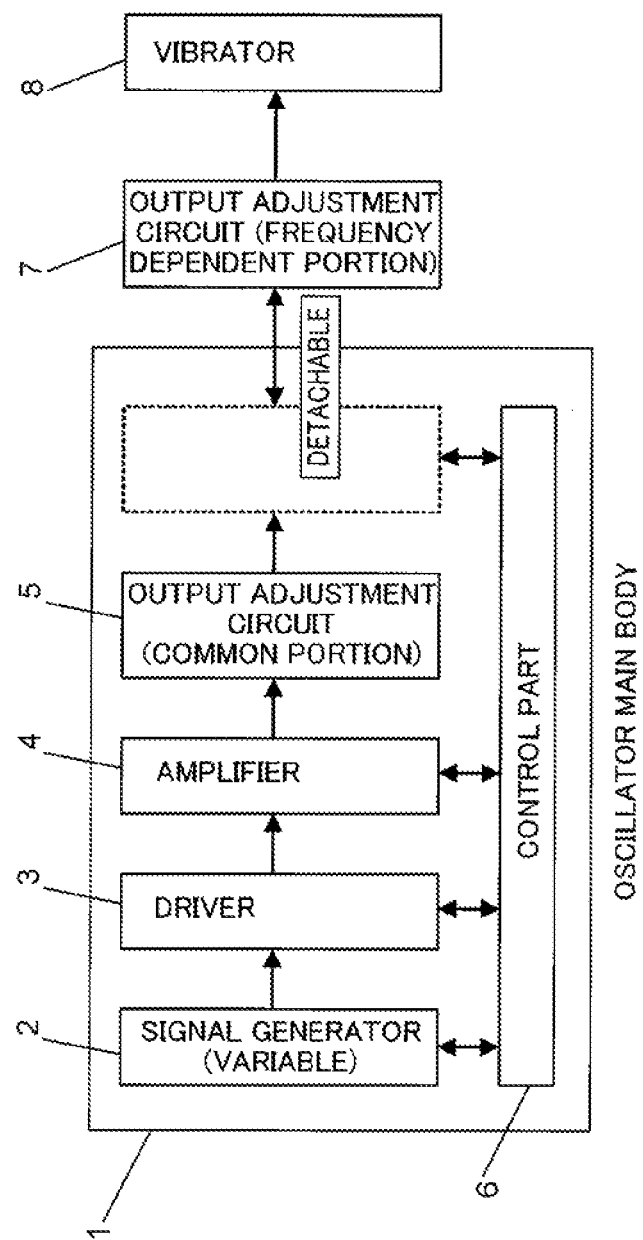
FIG. 1 is a schematic diagram illustrating a configuration of an ultrasonic transducer device according to a first embodiment of the present invention.

FIG. 1 is a schematic diagram illustrating a configuration of an ultrasonic transducer device according to a first embodiment of the present invention.

The ultrasonic transducer device illustrated in FIG. 1 is the one which constitutes apart of an ultrasonic washing machine, and is a device for applying ultrasonic transducer to cleaning fluid (not shown) when cleaning objects to be cleaned (not shown) by said cleaning fluid. This device comprises a generator main body 1, a second output adjustment circuit 7 detachably attached to this generator main body 1, and a transducer 8 connected to the second output adjustment circuit 7.

Said ultrasonic washing machine is an apparatus in which an ultrasonic vibration signal is generated from the generator main body 1, through the second output adjustment circuit 7, the ultrasonic vibration signal is transmitted to the transducer 8, and the ultrasonic vibration generated by the transducer 8 is applied to said cleaning fluid, thereby cleaning objects to be cleaned.

The generator main body 1 comprises a signal generator (variable) 2, and this signal generator 2 is a generator which generates signals applicable to a plurality of transducers each having a different frequency. The signal generator 2 is electrically connected to a driver 3. The driver 3 is electrically connected to an amplifier 4, and the amplifier 4 is electrically connected to a first output adjustment circuit 5. The first output adjustment circuit 5 includes circuits for a portion (common portion) which does not depend on a frequency of the transducer 8. Each of the signal generator 2, the driver 3 and the amplifier 4 is electrically connected to a control part 6.

When the second output adjustment circuit 7 is mounted in the generator main body 1, the second output adjustment circuit 7 is electrically connected to each of the first output adjustment circuit 5 and the control part 6. The second output adjustment circuit 7 includes circuits for a portion which depends on the frequency of the transducer 8. The generator main body 1 is composed of circuits or the like for a portion which does not depend on the frequency of the transducer 8.

Said ultrasonic transducer device is configured so that the signal generated by the signal generator 2 is driven by the driver 3, and is amplified by the amplifier 4, and is output-adjusted by the first and the second output adjustment circuits 5 and 7, and thereby, the ultrasonic vibration signal is outputted to the transducer 8, and is configured so that the control part 6 controls each of the signal generator 2, the driver 3, the amplifier 4 and the second output adjustment circuit 7.

The ultrasonic transducer device mentioned above is configured so that the second output adjustment circuit 7 and the transducer 8 may be detachable from the generator main body 1. Thereby, when changing the ultrasonic frequency in connection with cleaning recipe alterations, by changing only the second output adjustment circuit 7 and the transducer 8 for changing the transducer currently used with another one of a frequency different therefrom, it becomes possible to change the frequency. Therefore, it becomes possible to cope easily with frequent cleaning recipe alterations due to complication and refinement of a cleaning process.

In details, a circuit which needs to be altered greatly because electrical characteristics thereof differ largely depending on the frequency of the transducer 8 for changing the transducer 8 with the one of a frequency different therefrom is made to be formed as the second output adjustment circuit 7, and this second output adjustment circuit 7 together with the transducer 8 is made to be detachable. Therefore, for changing the transducer with the one of a frequency different therefrom, by changing only the second output adjustment circuit 7 and the transducer 8 without changing the generator main body 1, it becomes possible to change the frequency.

When the transducer 8 has trouble, for changing the faulty transducer with another one having the same frequency, it becomes possible to carry out repair thereof by changing only the second output adjustment circuit 7 and the transducer 8.

In details, even if a transducer type is the same, because variations in electrical characteristics depending on individual differences thereof exist, a circuit which requires adjustment for changing the transducer is included in the second output adjustment circuit (frequency dependent portion) 7. Therefore, by making detachable the second output adjustment circuit 7 together with the transducer 8, for changing the faulty transducer with another one, it becomes possible to carry out the repair thereof by changing only the second output adjustment circuit 7 and the transducer 8 without changing the generator main body 1.

While the first embodiment mentioned above is configured so that the transducer 8 is connected to the second output adjustment circuit 7, and the second output adjustment circuit 7 and the transducer 8 are detachable from the generator main body 1, it may be configured so that the transducer 8 may be detachably attached in the generator main body 1, and only the second output adjustment circuit 7 may be detachable from the generator main body 1. In this case, by mounting the second output adjustment circuit 7 in the generator main body 1, the second output adjustment circuit 7 will be electrically connected to each of the first output adjustment circuit 5, the control part 6 and the transducer 8.

Second Embodiment

Figure 2:
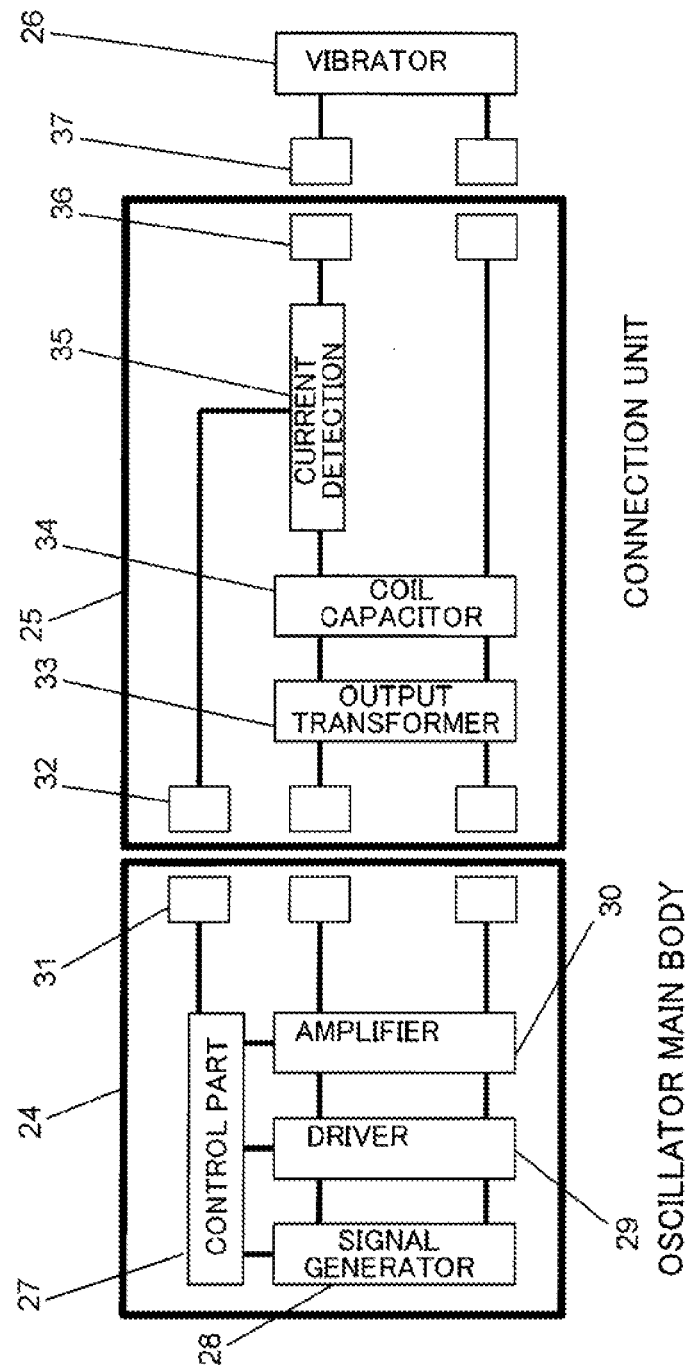
FIG. 2 is a schematic diagram illustrating a configuration of an ultrasonic transducer device according to a second embodiment of the present invention.

FIG. 2 is a schematic diagram illustrating a configuration of an ultrasonic transducer device according to a second embodiment of the present invention. This ultrasonic transducer device is the one which constitutes a part of an ultrasonic washing machine, and is a device for applying ultrasonic transducer to cleaning fluid (not shown) for cleaning objects to be cleaned (not shown) by said cleaning fluid. This device comprises a generator main body 24, a connection unit 25 detachably attached to this generator main body 24 and a transducer 26 detachably connected to this connection unit 25.

Said ultrasonic washing machine is an apparatus in which an ultrasonic vibration signal is generated from the generator main body 24 through the connection unit 25, the ultrasonic vibration signal is transmitted to the transducer 26, and the ultrasonic vibration generated by the transducer 26 is applied to said cleaning fluid, thereby cleaning objects to be cleaned.

The generator main body 24 includes a signal generator 28, and this signal generator 28 is a generator which generates a signal applicable to a plurality of transducers each having a different frequency. The signal generator 28 is electrically connected to a driver 29. The driver 29 is electrically connected to an amplifier 30, and the amplifier 30 is electrically connected to a connector 31. Each of the signal generator 28, the driver 29, the amplifier 30 and the connector 31 is electrically connected to a control part 27.

The connection unit 25 includes a connector 32 and this connector 32 is electrically connected to an output transformer 33 and a current detector 35. The output transformer 33 is electrically connected to a coil capacitor 34, and the coil capacitor 34 is electrically connected to each of a current detector 35 and a connector 36.

The generator main body 24 and the connection unit 25 are configured so as to be electrically connected by the connectors 31 and 32, and the connection unit 25 and the transducer 26 are configured so as to be electrically connected by connectors 36 and 37.

The connection unit 25 includes circuits for a portion which depends on a frequency of the transducer 26. The generator main body 24 is composed of circuits or the like for a portion which does not depend on the frequency of the transducer 26.

Said ultrasonic transducer device is configured so that the signal generated by the signal generator 28 may be driven by the driver 29, and may be amplified by the amplifier 30, and may be output-adjusted by the output transformer 33 and the coil capacitor 34, and thereby, the ultrasonic vibration signal may be outputted to the transducer 26, and is configured so that the control part 27 may control, with reference to a current value detected by the current detector 35, each of the signal generator 28, the driver 29 and the amplifier 30.

The ultrasonic transducer device mentioned above is configured so that the connection unit 25 and the transducer 26 may be detachable from the generator main body 24. Thereby, when changing the ultrasonic frequency in connection with cleaning recipe alterations, by changing only the connection unit 25 and the transducer 26 for changing the transducer currently used with another one of a frequency different therefrom, it becomes possible to change the frequency. Therefore, it becomes possible to cope easily with frequent cleaning recipe alterations due to the complication and refinement of the cleaning process.

In details, a circuit which needs to be altered greatly because the electrical characteristics thereof differ largely depending on the frequency of the transducer 26 for changing the transducer 26 with another one of a frequency different therefrom is the output transformer 33 and the coil capacitor 34. The connection unit 25 which includes these output transformer 33 and coil capacitor 34, together with the transducer 26, is made to be detachable from the generator main body 24. Therefore, for changing the transducer with another one of a frequency different therefrom, by changing only the connection unit 25 and the transducer 26 without changing the generator main body 24, it becomes possible to change the frequency.

When the transducer 26 has trouble, for changing the faulty transducer with another one having the same frequency, it becomes possible to carry out repair thereof by changing only the connection unit 25 and the transducer 26.

In details, even if a transducer type is the same, because variations in electrical characteristics depending on individual differences thereof exist, a circuit which requires adjustment for changing the transducer is the output transformer 33 and the coil capacitor 34. The connection unit 25 which includes these output transformer 33 and coil capacitor 34, together with the transducer 26, is made to be detachable from the generator main body 24. Therefore, for changing the faulty transducer with another one, it becomes possible to carry out the repair thereof by changing only the connection unit 25 and the transducer 26 without changing the generator main body 24.

Third Embodiment

Figure 3:
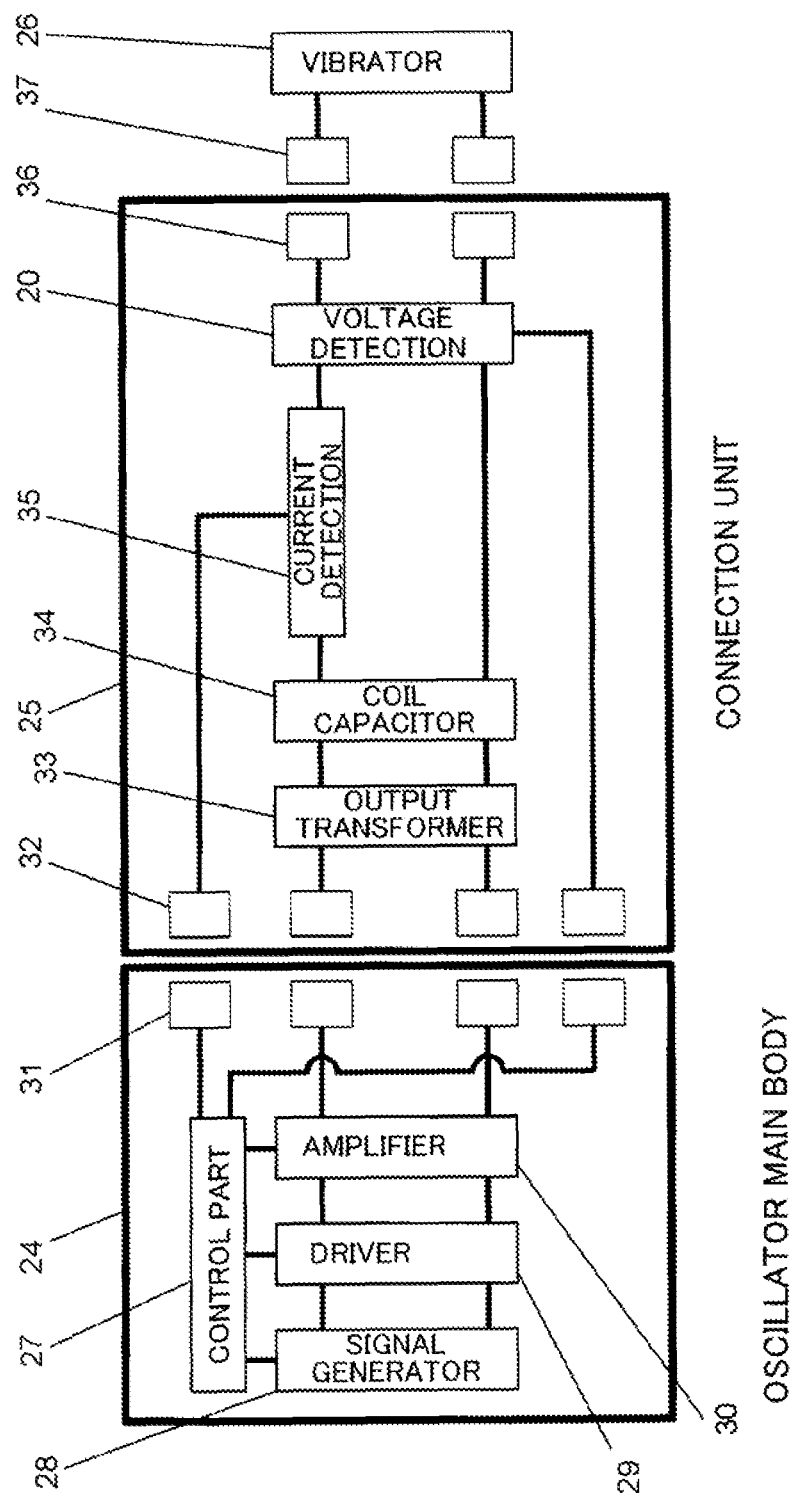
FIG. 3 is a schematic diagram illustrating a configuration of an ultrasonic transducer device according to a third embodiment of the present invention.

FIG. 3 is a schematic diagram illustrating a configuration of an ultrasonic transducer device according to a third embodiment of the present invention, and the same reference symbols are given to the same portions as FIG. 2, and only different portions will be described.

The connection unit 25 includes a voltage detector 20, and this voltage detector 20 is electrically connected to the connector 32.

Said ultrasonic transducer device is configured so that, with reference to a current value and a voltage value detected by the current detector 35 and the voltage detector 20 respectively, the control part 27 may control each of the signal generator 28, the driver 29 and the amplifier 30.

Also in the ultrasonic transducer device mentioned above, the same effect as that of the second embodiment can be acquired.

Since the connection unit 25 includes the voltage detector 20, it becomes possible for the control part 27 to control the signal generator 28, the driver 29 and the amplifier 30 more accurately.

Fourth Embodiment

Figure 4:
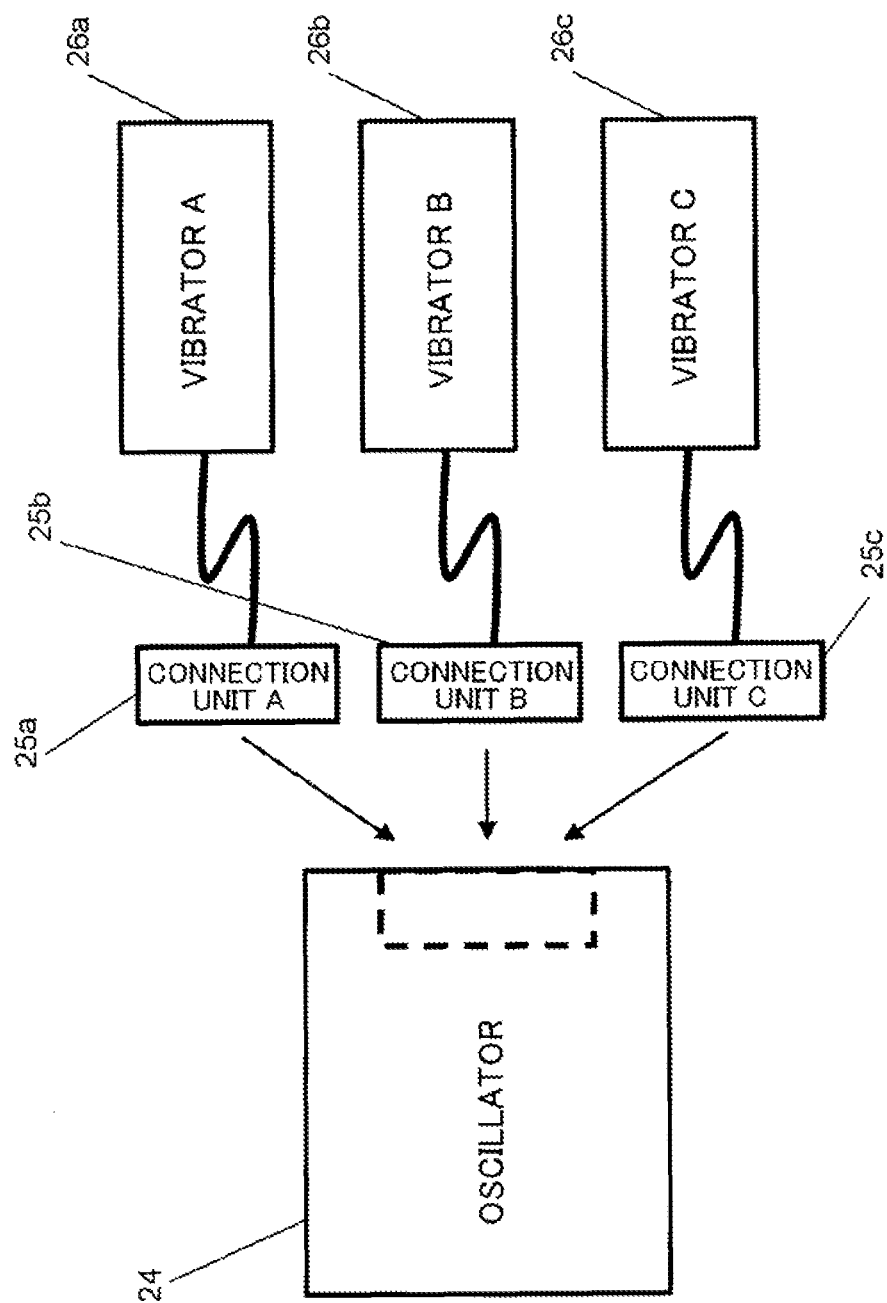
FIG. 4 is a schematic diagram illustrating a configuration of an ultrasonic transducer device by a fourth embodiment of the present invention.

FIG. 4 is a schematic diagram illustrating a configuration of an ultrasonic transducer device according to a fourth embodiment of the present invention, and the same reference symbols are given to the same portions as FIG. 2 and FIG. 3, and only different portions will be described.

A first transducer (transducer A) 26a which transduces at a first frequency, a second transducer (transducer B) 26b which transduces at a second frequency and a third transducer (transducer C) 26c which transduces at a third frequency are prepared. The first to the third frequencies are different from each other. To the first transducer 26a, a first connection unit (connection unit A) 25a is connected. To the second transducer 26b, a second connection unit (connection unit B) 25b is connected. To the third transducer 26c, a third connection unit (connection unit C) 25c is connected.

Also in the fourth embodiment mentioned above, the same effect as that of the second and third embodiments can be acquired.

Moreover, in the present embodiment, for applying ultrasonic transducer of the first frequency to the cleaning fluid, the first connection unit 25a is connected to the generator main body 24, and for applying ultrasonic transducer of the second frequency to the cleaning fluid, the second connection unit 25b is connected to the generator main body 24, and for applying ultrasonic transducer of the third frequency to the cleaning fluid, the third connection unit 25c is connected to the generator main body 24. Thereby, when changing the ultrasonic frequency, while, in conventional technology, also the generator main body must have been changed, in the present embodiment, without changing the generator main body, the frequency change can be realized by changing only the connection unit and the transducer.

Fifth Embodiment

Figure 5:
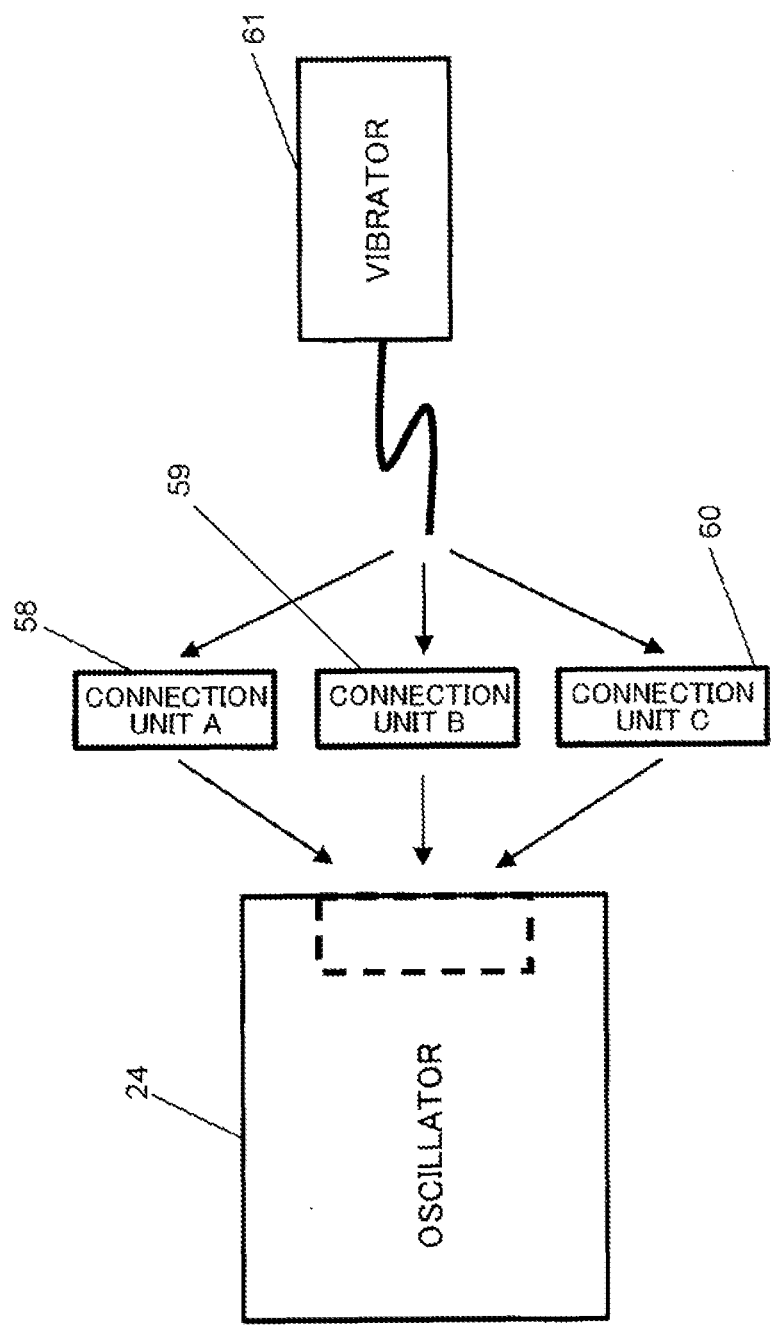
FIG. 5 is a schematic diagram illustrating a configuration of an ultrasonic transducer device according to a fifth embodiment of the present invention.

FIG. 5 is a schematic diagram illustrating a configuration of an ultrasonic transducer device according to a fifth embodiment of the present invention, and the same reference symbols are given to the same portions as FIG. 4, and only different portions will be described.

The ultrasonic transducer device illustrated in FIG. 5 is the one which carries out driving at three frequencies by a single transducer 61. A concept of carrying out such high order driving of a transducer like this is illustrated in FIG. 6.

Figure 6:
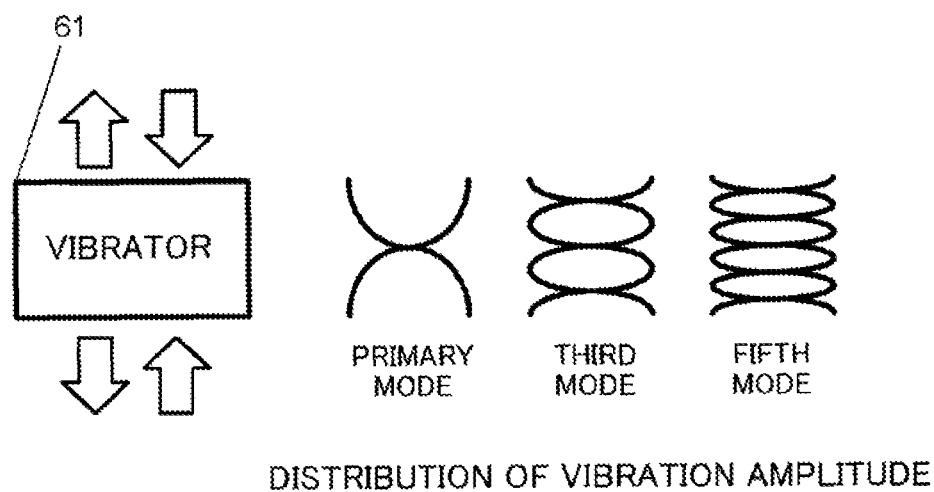
FIG. 6 is a conceptual diagram in which high order driving of a transducer is carried out.

A first connection unit (connection unit A) 58 illustrated in FIG. 5 is a connection unit for generating an ultrasonic vibration signal in the primary mode illustrated in FIG. 6, a second connection unit (connection unit B) 59 illustrated in FIG. 5 is a connection unit for generating an ultrasonic vibration signal in the third mode (third harmonic wave) illustrated in FIG. 6 and a third connection unit (connection unit C) 60 illustrated in FIG. 5 is a connection unit for generating an ultrasonic vibration signal in the fifth mode (fifth harmonic wave) illustrated in FIG. 6.

The first to the third connection units 58 to 60, respectively, are configured detachably and connectably from/to the transducer 61.

Also in the fifth embodiment mentioned above, the same effect as that of the second and third embodiments can be acquired.

Moreover, in the present embodiment, for applying ultrasonic transducer having a frequency (for example, 30 kHz) in the primary mode to the cleaning fluid, the first connection unit 58 is connected to the generator main body 24, and for applying ultrasonic transducer having a frequency (for example, 90 kHz) in the third mode to the cleaning fluid, the second connection unit 59 is connected to the generator main body 24, and for applying ultrasonic transducer having a frequency (for example, 150 kHz) in the fifth mode to the cleaning fluid, the third connection unit 60 is connected to the generator main body 24. Thereby, when changing the ultrasonic frequency to any of frequencies of the primary mode, the third mode and the fifth mode, while in conventional technology, also the generator main body must be changed, in the present embodiment, without changing the generator main body, the frequency change can be realized by changing only the connection unit.

While the fifth embodiment mentioned above makes the transducer 61 common when the transducer is transduced at each of the frequencies of the primary mode, the third mode and the fifth mode, the transducers when being transduced at each of the frequencies of the primary mode, the third mode and the fifth mode each may be prepared separately.

While the fifth embodiment mentioned above is configured so as to make the transducer transduce at three frequencies of the primary mode, the third mode and the fifth mode, it is possible also to be configured so as to make the transducer transduce at four or more frequencies of the primary mode, the third mode, the fifth mode, the seventh mode, . . . .

Sixth Embodiment

Figure 7:
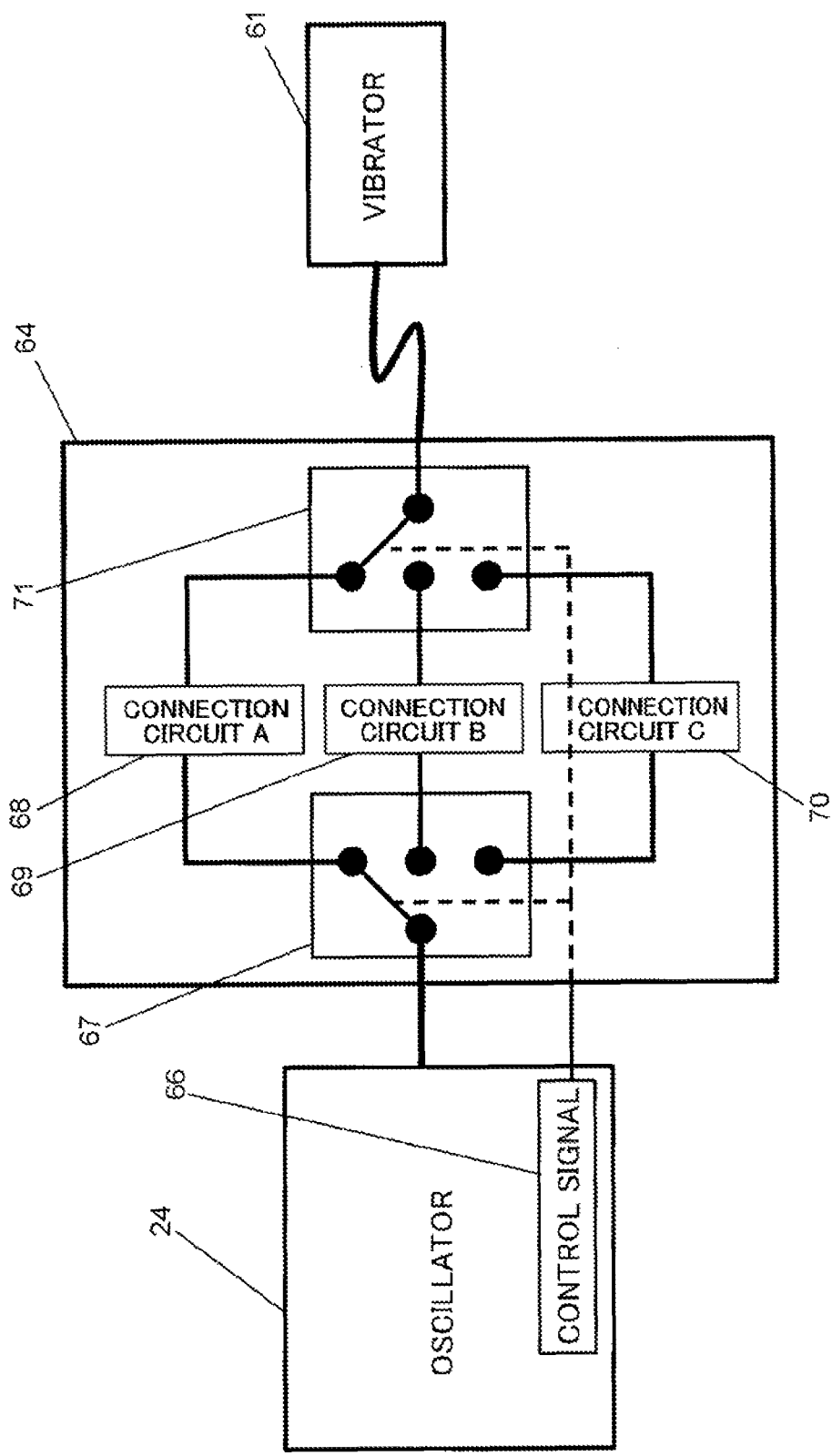
FIG. 7 is a schematic diagram illustrating a configuration of an ultrasonic transducer device according to a sixth embodiment of the present invention.
Figure 8:
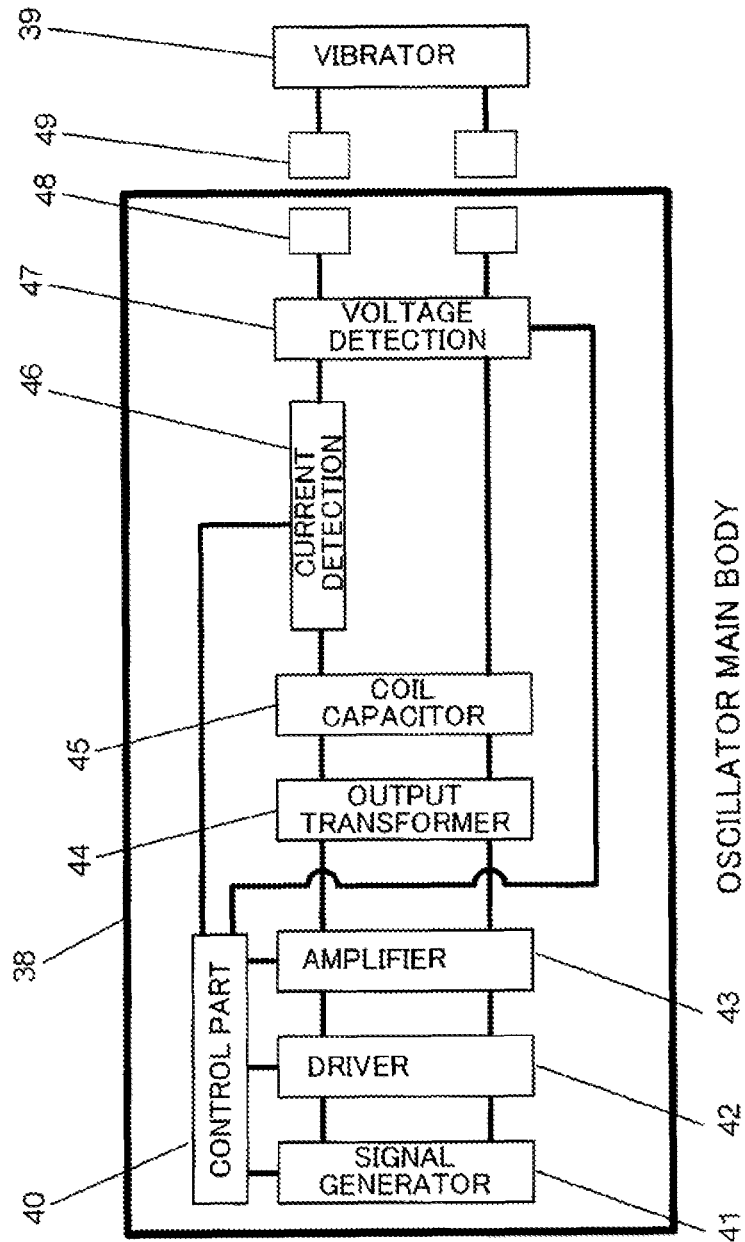
FIG. 8 is a schematic diagram illustrating a configuration of a conventional ultrasonic transducer device.

FIG. 7 is a schematic diagram illustrating a configuration of an ultrasonic transducer device according to a sixth embodiment of the present invention, and the same reference symbols are given to the same portions as FIG. 5, and only different portions will be described.

A connection unit 64 is electrically connected to the generator main body 24. The connection unit 64 includes a first connection circuit (connection circuit A) 68, a second connection circuit (connection circuit B) 69, a third connection circuit (connection circuit C) 70 and a change-over switch having a first and a second change-over switch 67, 71.

Each of the first and second change-over switches 67, 71 is electrically connected to the generator main body 24, and change-over in the switch is controlled by a control signal 66 from a control part of the generator main body 24. The second change-over switch 71 is electrically connected to the transducer 61.

The first change-over switch 67 is electrically connected to each of the first to the third connection circuits 68 to 70, and each of the first to the third connection circuits 68 to 70 is electrically connected to the second change-over switch 71.

That is, it is controlled by the first and the second change-over switches 67 and 71 whether each of the generator main body 24 and the transducer 61 is connected to any of the first to the third connection circuits 68 to 70.

Each of the first to the third connection circuits 68 to 70 is a circuit which causes the transducer 61 to transduce at a mutually different frequency like the fifth embodiment. In details, the first connection circuit 68 is a circuit for generating the ultrasonic vibration signal in the primary mode illustrated in FIG. 6, and the second connection circuit 69 is a circuit for generating the ultrasonic vibration signal in the third mode (third harmonic wave) illustrated in FIG. 6, and the third connection circuit 70 is a circuit for generating the ultrasonic vibration signal in the fifth mode (fifth harmonic wave) illustrated in FIG. 6.

Also in the sixth embodiment mentioned above, the same effect as that of the fifth embodiment can be acquired.

In details, for applying the ultrasonic transducer having the frequency (for example, 30 kHz) in the primary mode to the cleaning fluid, the first connection circuit 68 is connected to the generator main body 24, and for applying the ultrasonic transducer having the frequency (for example, 90 kHz) in the third mode to the cleaning fluid, the second connection circuit 69 is connected to the generator main body 24, and for applying the ultrasonic transducer having the frequency (for example, 150 kHz) in the fifth mode to the cleaning fluid, the third connection circuit 70 is connected to the generator main body 24. Thereby, when changing the ultrasonic frequency to any of frequencies of the primary mode, the third mode and the fifth mode, while in conventional technology, also the generator main body must be changed, in the present embodiment, without changing the generator main body, the frequency change can be realized only by controlling the change-over switch by the control signal 66.

The present invention is not limited to embodiments mentioned above, and can be carried out by modifying variously without departing from the spirits and the scope of the present invention. For example, the present invention can also be carried out by changing the change-over switch in the sixth embodiment into a relay.

The present invention can also be carried out by combining mutually the embodiments mentioned above, and for example, can also be carried out by combining the fourth embodiment and sixth embodiment. In details, connecting any of the first to the third connection units to the generator main body 24 in the fourth embodiment can be realized by switching over the connection units by a change-over switch.

DESCRIPTION OF SYMBOLS 1, 24 . . . GENERATOR MAIN BODY
2, 28 . . . SIGNAL GENERATOR
3, 29 . . . DRIVER
4, 30 . . . AMPLIFIER
5 . . . FIRST OUTPUT ADJUSTMENT CIRCUIT
6, 27 . . . CONTROL PART
7 . . . SECOND OUTPUT ADJUSTMENT CIRCUIT
8, 26, 61 . . . TRANSDUCER
20 . . . VOLTAGE DETECTOR
25, 64 . . . CONNECTION UNIT
25A TO 25C, 58 TO 60 . . . FIRST TO THIRD CONNECTION UNITS (CONNECTION UNITS A TO C)
26A TO 26C . . . FIRST TO THIRD TRANSDUCERS (TRANSDUCERS A TO C)
31, 32, 36, 37 . . . CONNECTOR
33 . . . OUTPUT TRANSFORMER
34 . . . COIL CAPACITOR

35 ... CURRENT DETECTOR
66 ... CONTROL SIGNAL
67 ... FIRST CHANGE-OVER SWITCH
68 TO 70 ... FIRST TO THIRD CONNECTION CIRCUITS (CONNECTION CIRCUITS A TO C)
71 ... SECOND CHANGE-OVER SWITCH

The invention claimed is:

1. An ultrasonic transducer device component comprising an output adjustment circuit for use in applying ultrasonic vibration from a transducer to cleaning fluid for cleaning objects, the output adjustment circuit being formed detachably in a generator main body for causing the transducer to generate an ultrasonic vibration signal, wherein the output adjustment circuit includes a circuit which depends on a frequency of the transducer, the output adjustment circuit being configured to change the transducer with another transducer having a different frequency, and wherein the circuit comprises:

an output transformer for adjusting an output of the ultrasonic vibration signal;

a coil capacitor electrically connected to the output transformer; and a current detector electrically connected to the coil capacitor.

* * * * *